(12) United States Patent
Stevens-Wright

(10) Patent No.: US 7,922,714 B2
(45) Date of Patent: Apr. 12, 2011

(54) METHOD AND APPARATUS FOR SELECTING OPERATING PARAMETER VALUES IN ELECTROPHYSIOLOGY PROCEDURES

(75) Inventor: Debbie Stevens-Wright, North Andover, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 535 days.

(21) Appl. No.: 10/551,294

(22) PCT Filed: Mar. 29, 2004

(86) PCT No.: PCT/US2004/009620
§ 371 (c)(1),
(2), (4) Date: Nov. 22, 2006

(87) PCT Pub. No.: WO2004/086995
PCT Pub. Date: Oct. 14, 2004

(65) Prior Publication Data
US 2007/0167940 A1    Jul. 19, 2007

Related U.S. Application Data

(60) Provisional application No. 60/458,489, filed on Mar. 28, 2003, provisional application No. 60/458,490, filed on Mar. 28, 2003, provisional application No. 60/458,491, filed on Mar. 28, 2003, provisional application No. 60/458,643, filed on Mar. 28, 2003, provisional application No. 60/458,856, filed on Mar. 28, 2003.

(51) Int. Cl.
*A61B 18/10* (2006.01)

(52) U.S. Cl. ............................................ 606/34; 606/41

(58) Field of Classification Search .............. 606/32–35, 606/41, 42, 48–50
See application file for complete search history.

(56) References Cited

U.S. PATENT DOCUMENTS

| | | | |
|---|---|---|---|
| 5,837,001 A | 11/1998 | Mackey | |
| 5,840,030 A | 11/1998 | Breyer et al. | |
| 5,893,848 A * | 4/1999 | Negus et al. | 606/41 |
| 6,022,347 A | 2/2000 | Lindenmeier et al. | |
| 6,183,468 B1 | 2/2001 | Swanson et al. | |

(Continued)

FOREIGN PATENT DOCUMENTS

WO    WO 02/100255 A2    12/2002

OTHER PUBLICATIONS

Jain et al; Annals of Biomedical Engineering, vol. 28, pp. 1075-1084, 2000; "A Three-Dimensional Finite Element Model of Radiofrequency Ablation with Blood Flow and it Experimental Validation".*

Zhang et al; IEEE Transaction of Biomedical Engineering, vol. 20, No. 2, Feb. 2003; "Nontact Radio-Frequency Ablation for Obtaining Deeper Lesions".*

(Continued)

*Primary Examiner* — Michael Peffley
(74) *Attorney, Agent, or Firm* — Wolf, Greenfield & Sacks, P.C.

(57) ABSTRACT

Methods of selecting operating parameter values for tissue ablation procedures are disclosed. Energy supply parameters may be selected based on inputs such as fluid flow rate, impedance, and the distance from an ablation electrode surface to a target tissue surface. The distance to place an ablation electrode surface from a target tissue surface may be selected based on various operating parameter values and/or operating condition values. Operating curves, lookup tables, or processors may be used to select operating parameter values.

20 Claims, 8 Drawing Sheets

U.S. PATENT DOCUMENTS

| | | | |
|---|---|---|---|
| 6,264,653 | B1 | 7/2001 | Falwell |
| 6,409,722 | B1 * | 6/2002 | Hoey et al. .................. 606/34 |
| 6,451,015 | B1 * | 9/2002 | Rittman et al. .............. 606/34 |
| 6,575,969 | B1 * | 6/2003 | Rittman et al. .............. 606/41 |
| 6,666,862 | B2 | 12/2003 | Jain et al. |
| 7,422,585 | B1 * | 9/2008 | Eggers et al. ................ 606/41 |
| 2002/0002372 | A1 | 1/2002 | Francischelli et al. |
| 2002/0123749 | A1 | 9/2002 | Jain |
| 2002/0169445 | A1 * | 11/2002 | Jain et al. .................... 606/41 |
| 2003/0195501 | A1 | 10/2003 | Sherman et al. |
| 2004/0015163 | A1 | 1/2004 | Buysse et al. |

OTHER PUBLICATIONS

International Search Report dated, Aug. 25, 2004 from International Application No. PCT/US2004/009620.

Jain, et al.; Annals of Biomedical Engineering, vol. 28, pp. 1075-1084, 2000; "A Three-Dimensional Finite Element Model of Radiofrequency Ablation with Blood Flow and Its Experimental Validation".

Zhang, et al.; IEEE Transaction on Biomedical Engineering, vol. 50, No. 2, Feb. 2003 "Noncontact Radio-Frequency Ablation for Obtaining Deeper Lesions".

* cited by examiner

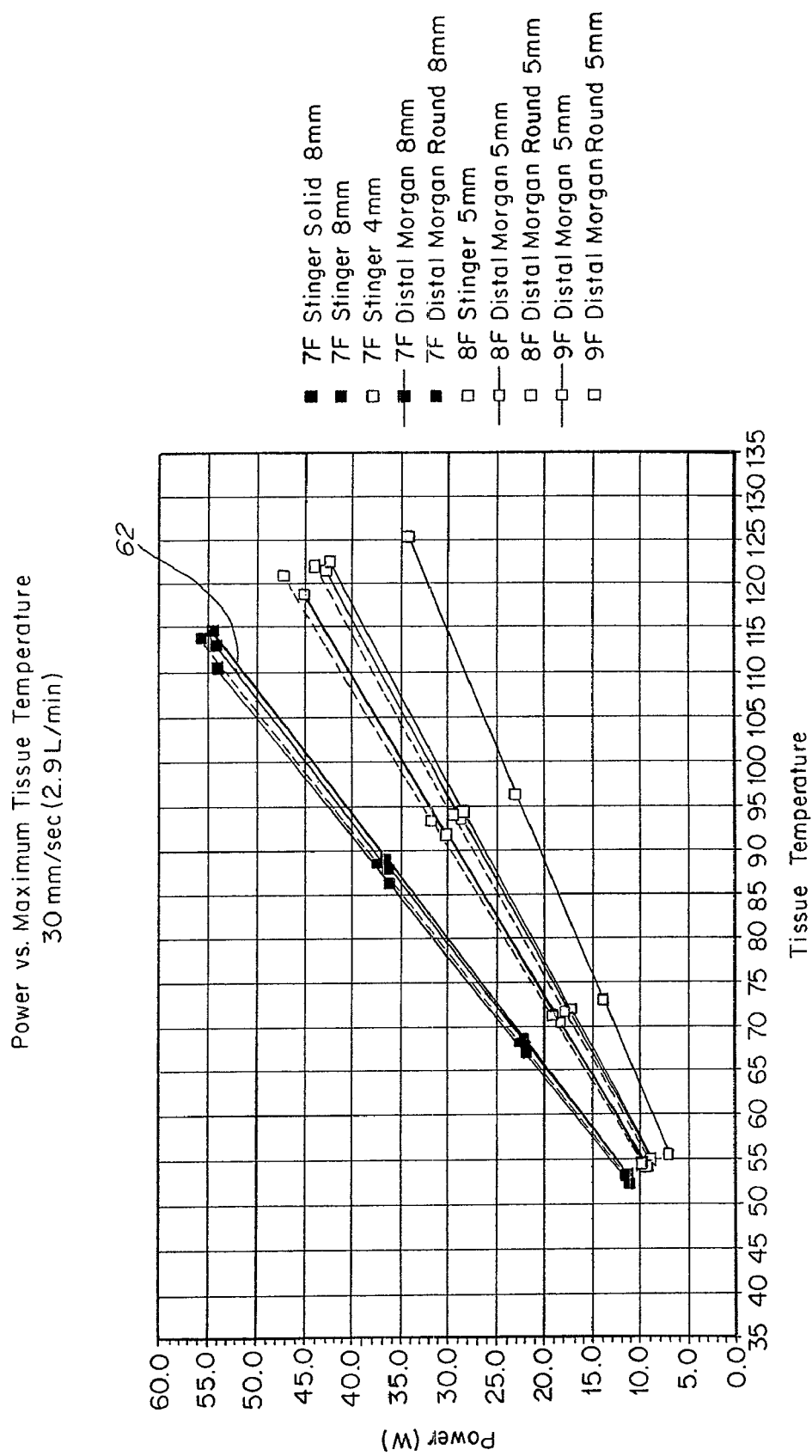

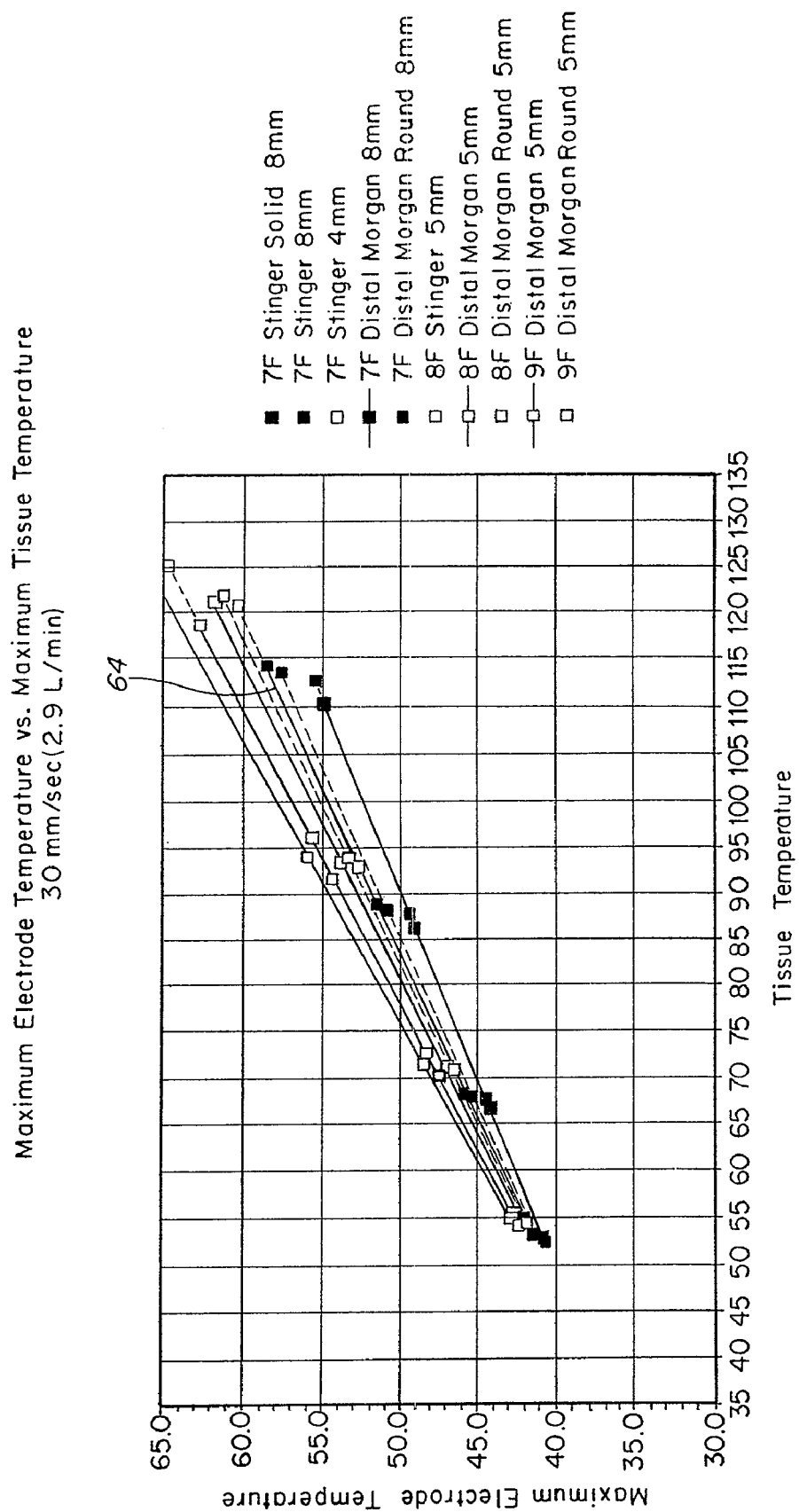

METHOD AND APPARATUS FOR SELECTING OPERATING PARAMETER VALUES IN ELECTROPHYSIOLOGY PROCEDURES

RELATED APPLICATIONS

This application is a national stage filing under 35 U.S.C. §371 of International Application No. PCT/US04/09620, filed Mar. 29, 2004. International Application No. PCT/US04/09620 claims priority under 35 U.S.C. §119(e) to U.S. Provisional Application Ser. No. 60/458,489, entitled "Electrode for Electrophysiology Catheter Having an Eccentric Surface", filed on Mar. 28, 2003, U.S. Provisional Application Ser. No. 60/458,490, entitled "Electrophysiology Catheter Allowing Adjustment Between Electrode and Tissue Gap", filed on Mar. 28, 2003, U.S. Provisional Application Ser. No. 60/458,491, entitled "Shape Shifting Electrode Geometry for Electrophysiology Catheters", filed on Mar. 28, 2003, U.S. Provisional Application Ser. No. 60/458,643, entitled "Method and Apparatus for Selecting Temperature/Power Set Points in Electrophysiology Procedures", filed on Mar. 28, 2003, and U.S. Provisional Application Ser. No. 60/458,856, entitled "Catheter Tip/Electrode Junction Design for Electrophysiology Catheters" filed on Mar. 28, 2003, all five of which are each incorporated herein by reference in their entireties.

BACKGROUND OF INVENTION

1. Field of Invention

The invention relates to medical devices and methods for performing ablation procedures. More particularly, the invention relates to methods and apparatus for selecting operating parameter values for the performance of ablation procedures.

2. Discussion of Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete 'fence' around a circuit or tissue region is not always required in order to block the propagation of the arrhythmia; in many cases simply increasing the propagation path length for a signal may be sufficient. Conventional means for establishing such lesion 'fences' include a multiplicity of point-by-point lesions, dragging a single electrode across tissue while delivering energy, or creating an enormous lesion intended to inactivate a substantive volume of myocardial tissue.

In creating lesions, care is taken to limit blood coagulation and tissue charring and desiccation. These undesirable effects can occur if temperatures in the tissue or blood rise to 100° C. In addition to effects on the blood and tissue, temperatures of 100° C. or more at the electrode-tissue interface can foul an electrode due to tissue charring. Various strategies are employed to maintain temperatures below 100° C. Electrode cooling (active and/or passive) is one strategy employed in an attempt to cool the tissue at the tissue surface where temperatures can often be the highest, thereby allowing a more even temperature distribution in the tissue. Other strategies include limiting the power applied to the electrode based on predetermined estimates of appropriate power levels, and reducing the power applied to the electrode in response to feedback signals from the electrode or other sensors. Reduced power application, however, is balanced with the desirability of raising the temperature of an adequate volume of tissue above its viability temperature and the benefits of reducing total procedure time.

There exists a need to improve the delivery of energy to tissue to form lesions without exceeding temperatures that result in charring, desiccation or blood coagulation.

SUMMARY OF INVENTION

Embodiments of the present invention encompass apparatus and method for creating lesions in heart tissue (ablating) to create a region of necrotic tissue which serves to disable the propagation of errant electrical impulses caused by an arrhythmia. Embodiments of the present invention also encompass apparatus and methods for selecting values for operating parameters to be used in systems and apparatus configured to create lesions in heart tissue.

According to one embodiment, a method of selecting an operating parameter value for supplying energy to an ablation electrode comprises receiving a first signal representing a value of a fluid flow rate, receiving a second signal representing a value of an impedance, receiving a third signal representing a value of a distance from an ablation electrode surface to a target tissue surface, and selecting a value for an operating parameter for supplying energy to the ablation electrode as a function of the first, second and third signals.

According to another embodiment, a method of ablating biological tissue to form a lesion comprises positioning an ablation electrode having a surface at an ablation site, receiving a first signal representing a value of a fluid flow rate, receiving a second signal representing a value of an impedance, receiving a third signal representing a value of a distance from the ablation electrode surface to a target tissue surface, selecting a value for an ablation operating parameter as a function of the first, second and third signals, and operating the ablation electrode at the selected operating parameter value to ablate biological tissue.

According to a further embodiment, a system comprises a catheter having a shaft, an ablation electrode positioned on the shaft, an energy supply, and an input interface. The input interface is configured to receive a signal representing a value of a fluid flow rate, a signal representing a value of an impedance, and a signal representing a value of a distance from an electrode surface to a target tissue surface. The system also comprises a processor operatively connected to the input interface and programmed to select an operating parameter value for supplying energy to the ablation electrode with the energy supply, the selection being a function of the three signals received by the input interface, and an output interface operatively connected to the processor and configured to provide the selected operating parameter value.

According to another embodiment, a computer-readable medium has instructions stored thereon that, as a result of being executed by a computer, instruct the computer to perform a method comprising receiving a first signal representing a value of a fluid flow rate, receiving a second signal representing a value of an impedance, receiving a third signal representing a value of a distance from an ablation electrode surface to a target tissue surface, and selecting a value for an operating parameter for supplying energy to the ablation electrode as a function of the first, second and third signals.

According to a further embodiment, a system comprises a catheter having a shaft, an ablation electrode positioned on the shaft, an energy supply, and an input interface. The input interface is configured to receive a first signal representing a value of a fluid flow rate, a second signal representing a value of an impedance, and a third signal representing a value of a distance from an electrode surface to a target tissue surface. The system further comprises means for selecting an operating parameter value for supplying energy to the ablation electrode with the energy supply, the means for selecting using the first, second and third signals, and an output interface configured to provide the selected operating parameter value.

According to another embodiment, a method of selecting an operating parameter value for transmitting energy to tissue comprises receiving a first signal representing a value of a fluid flow rate near the tissue, receiving a second signal representing a value of an impedance, and selecting a value for a distance to set an ablation electrode surface apart from a target tissue surface as a function of the first and second signals.

According to a further embodiment, a method of selecting an operating parameter value for transmitting energy to tissue comprises receiving a first signal representing a value of a fluid flow rate near the tissue, and selecting a value for a distance to set an ablation electrode surface apart from a target tissue surface as a function of the first signal.

According to another embodiment, a method of selecting an operating parameter value for supplying energy to an ablation electrode comprises receiving a first signal representing a value of a fluid flow rate near the tissue, receiving a second signal representing a value of a distance from an ablation electrode surface to a target tissue surface, and selecting a value for an operating parameter for supplying energy to an ablation electrode as a function of the first and second signals.

According to a further embodiment, a method of selecting an operating parameter value for transmitting energy to tissue comprises receiving a first signal representing a value of a fluid flow rate near the tissue, receiving a second signal representing a value of a distance from an ablation electrode surface to a target tissue surface, and selecting a value for an electrode impedance as a function of the first and second signals.

According to another embodiment, a method of establishing a relationship between operating condition values and a value for an ablation operating parameter comprises: providing a plurality of data sets comprising a value of fluid flow, a value of impedance, and a value of distance from an ablation electrode surface to a target tissue surface; for each of the plurality of data sets, performing at least two analyses of an ablation electrode transmitting energy to biological tissue using a numerical model, the at least two analyses corresponding to at least two different values of an ablation operating parameter, and wherein the numerical model uses each of the three values of the data set; and based on the results of the at least two analyses for each data set, establishing a relationship between each data set and a corresponding value for the ablation operating parameter.

According to a further embodiment, a method of establishing a relationship between operating condition values and values for ablation operating parameters comprises providing a data set comprising values of operating conditions, and performing a first analysis of a numerical model, the numerical model modeling transmission of energy to biological tissue and the first analysis using the values of the operating conditions, a first value for an energy supply operating parameter and a first value for a distance from an ablation electrode surface to a target tissue surface. The method further comprises performing a second analysis of the numerical model using the values of the operating conditions and a second value for the distance from the ablation electrode surface to the target tissue surface. The method further comprises, based on the results of the first and second analyses, establishing a relationship between the data set and corresponding values for the energy supply operating parameter and the distance from the ablation electrode surface to the target tissue surface.

BRIEF DESCRIPTION OF DRAWINGS

The accompanying drawings are not intended to be drawn to scale. In the drawings, like components that are illustrated in various figures are represented by a like numeral. For purposes of clarity, not every component may be labeled in every drawing. In the drawings:

FIG. 10 illustrates results of model analyses for an exemplary ablation procedure model;

FIG. 11 illustrates further results of model analyses for an exemplary ablation procedure model;

DETAILED DESCRIPTION

Figure 1:
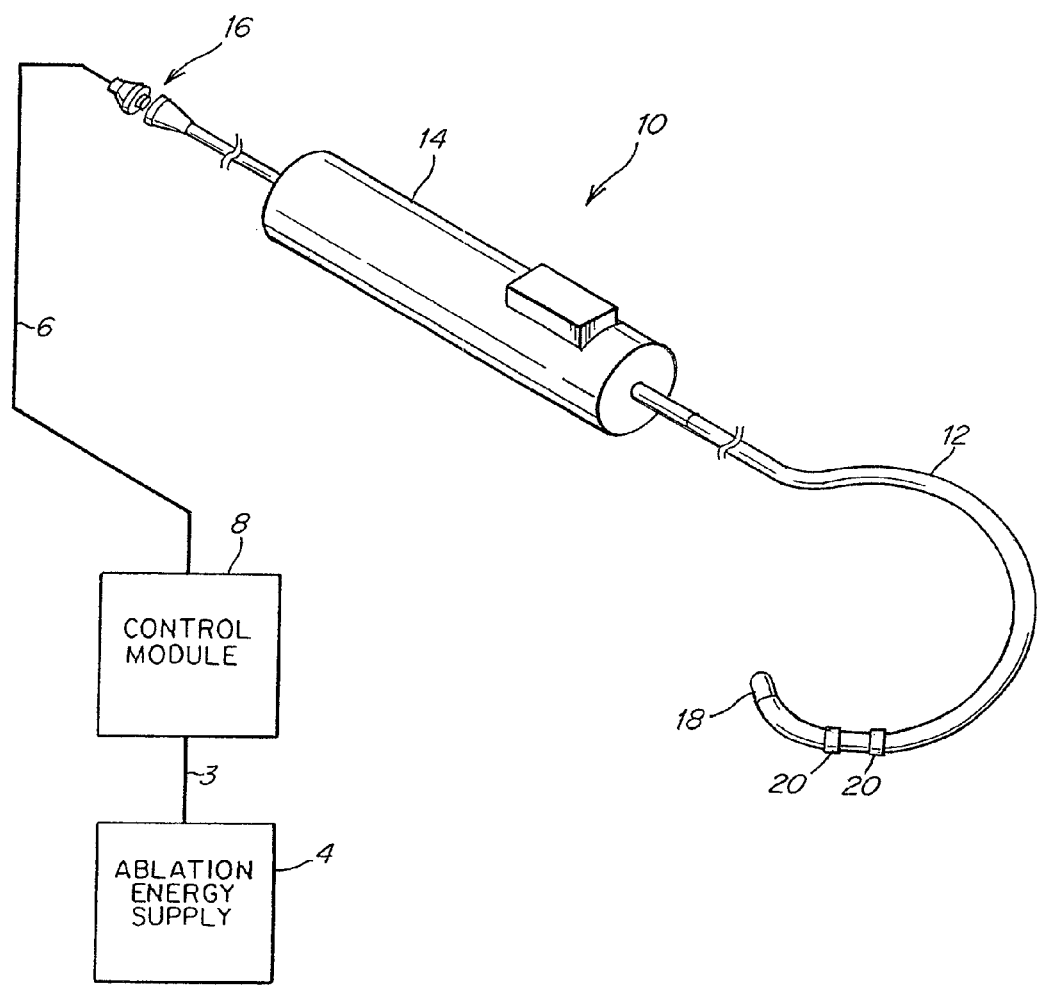
FIG. 1 illustrates a catheter system in accordance with embodiments of the present invention.

This invention is not limited in its application to the details of construction and the arrangement of components and acts set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

During ablation procedures, one objective is to raise tissue temperatures above the tissue's viability temperature without allowing the temperatures to exceed a temperature of approximately 100° C. As described above, excessive temperatures can cause tissue charring, tissue desiccation, and/or blood coagulation. The shape and impedance of an electrode selected to perform ablation and the characteristics of the energy supplied to the electrode significantly affect the result of an ablation procedure. Difficulties associated with monitoring the ablation procedure and the different operating conditions encountered during ablation procedures can, in some cases, limit the ability to produce a sizeable lesion without risking undesirable temperatures.

Modeling of ablation procedures, such as numerical modeling, may be used to estimate the outcomes of using selected values for various operating parameters of an ablation process. By performing analyses of a numerical model, different values of electrode power or electrode voltage can be tested for the effects on tissue or blood temperature and lesion size. By analyzing the model for multiple operating parameter values, relationships can be established between operating conditions, such as blood flow rate, and operating parameter values, such as the power to be applied to the electrode.

Applicants have recognized that in many instances positioning the ablation electrode at a distance from the target tissue surface can improve lesion size by forming a more even distribution of temperature within the tissue. Modeling of tissue ablation including the modeling of a distance between an ablation electrode and a target tissue surface can provide improved ablation procedure control. By allowing the distances from the electrode to the tissue surface to be factored into ablation modeling, improved ablation results may be obtained by selecting more appropriate operating parameter values. In one embodiment of the invention, values for blood flow rate, impedance and distance from an electrode to a target tissue surface are used to select an operating parameter value for energy supply to the electrode. Optimization strategies also may be employed in conjunction with multiple analyses of the model to determine improved operating parameter values.

System Overview

Reference is now made to FIG. 1, which figure illustrates an overview of an ablation catheter system in accordance with embodiments of the present invention. The system includes a catheter 10 having a shaft portion 12, a control handle 14, and a connector portion 16. A control module 8 is connected to connector portion 16 via cable 6. Ablation energy supply 4 may be connected to control module 8 via cable 3. Control module 8 is used to control ablation energy provided by ablation energy supply 4 to catheter 10. Although illustrated as separate devices, ablation energy supply 4 and control module 8 could be incorporated into a single device.

In this description, various aspects and features of embodiments of the present invention will be described. The various features of the embodiments of the invention are discussed separately for clarity. One skilled in the art will appreciate that the features may be selectively combined in a device depending upon the particular application. Furthermore, any of the various features may be incorporated in a catheter and associated methods of use for ablation procedures.

Catheter Overview

Catheter 10 may include a distal tip electrode 18 and/or one or more ring electrodes 20. Ring electrodes 20 may be arranged on shaft 12 such that their outer surfaces are flush with the catheter surface, or they may be arranged such that the electrode outer surfaces have diameters that are larger or smaller than the shaft diameter. In some embodiments, ring electrodes 20 may be adjustable in size or shape, may be moveable along shaft 12, or may be asymmetric with respect to shaft 12.

Distal tip electrode 18 may be affixed to the distal tip of shaft 12 such that it does not move relative to the distal tip, or distal tip electrode 18 may be moveable relative to shaft 12. Catheter 10 may be a steerable device. FIG. 1 illustrates the distal tip portion 18 being deflected by the mechanism contained within control handle 14. Control handle 14 may include a rotatable thumb wheel (not shown) which can be used by a user to deflect the distal end of the catheter. The thumb wheel (or any other suitable actuating device) is connected to one or more pull wires which extend through shaft portion 12 and are connected to the distal end 18 of the catheter at an off-axis location, whereby tension applied to one or more of the pull wires causes the distal portion of the catheter to curve in a predetermined direction or directions.

Figure 2:
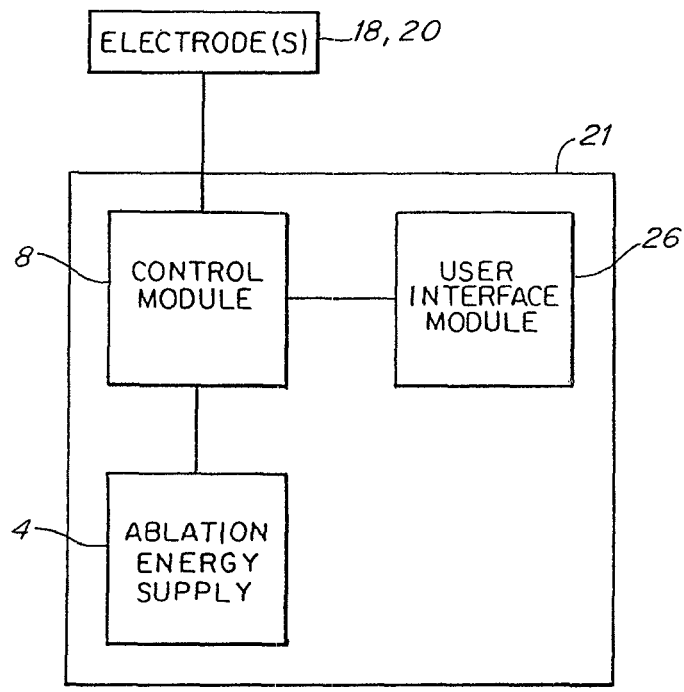
FIG. 2 illustrates details of a control system according to one embodiment of the invention.

Referring now to FIG. 2, one embodiment of a control system 21 is illustrated. The various modules of control system 21 may be combined in a single device or unit, or various modules may be separate units that communicate with one another either automatically or with human intervention.

An ablation energy supply 4 is provided to supply the electrode(s) 18, 20 with energy in the form of, for example, RF, microwave, DC, ultrasound, or laser radiation.

Control module 8 controls the energy supplied to the electrode(s) 18, 20 by regulating various energy supply parameters. For example, for some ablation procedures, control module 8 may sustain the supplied energy at a constant power, a constant voltage or a constant current. In some embodiments, control module 8 may receive feedback (such as electrode temperature) from electrode(s) 18, 20 and vary the energy supplied based on the feedback. In other ablation procedures, control module 8 may vary any of the above parameters or control other parameters such as frequency, pulse rate, amplitude, duty cycle, wave shape, or any other suitable parameter. Control module 8 may be embodied in hardware, firmware, software, or any suitable combination thereof. Control system 21 may be attachable to catheter 10 via cable 6 and connector portion 16, or portions of control system 21 may be physically incorporated into control handle 14.

A user interface 26 may be provided to facilitate user interaction with control module 8. User interface 26 may include a keypad, a touch screen, a set of input buttons or switches, a voice-activated interface, or any other suitable interface for accepting input from a user or for providing output to a user. User interface 8 may be an operative connection to a separate device (not shown) such that control module 8 is able to communicate with the separate device.

Figure 3:
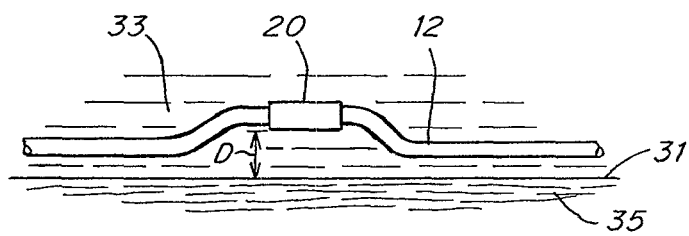
FIG. 3 illustrates a ring electrode positioned at a distance from a tissue surface.

As illustrated in FIG. 3, ring electrode 20 may be arranged on shaft 12 such that it is held a distance D from a tissue surface 31. With applied RF energy, ring electrode 20 generates a potential field around ring electrode 20 and heats the surrounding material, such as blood 33 and tissue 35, based on the properties of that material. Blood flow, if present, may cool tissue surface 31 and ring electrode 20.

In this embodiment, shaft 12 is configured with a bent shaft to provide a distance D between electrode 20 and tissue surface 31, but in other embodiments, ring electrode 20 itself may be constructed and arranged to provide a distance between tissue surface 31 and ring electrode 20 on a straight shaft. In some embodiments, distance D is fixed for a given electrode or shaft, and in other embodiments, the electrode, shaft, or other control device may be used to adjust distance D. In further embodiments, movement of ring electrode 20 along shaft 12 may adjust distance D.

Figure 4:
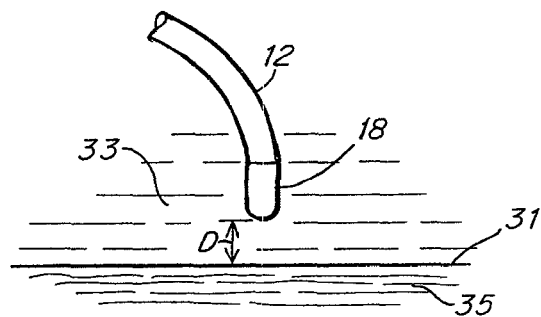
FIG. 4 illustrates a distal tip electrode positioned at a distance from a tissue surface.

FIG. 4 illustrates distal tip electrode 18 separated by distance D from tissue surface 31. With a shaft 12 that is steerable, distance D may be varied. In other embodiments, other suitable mechanisms for controlling distance D may be employed. For example, distal tip electrode 18 or ring electrode 20 may be configured for shape changes which allow for adjustment of distance D. Changes to the shapes of electrodes 18, 20 also may alter electrode impedance values and therefore the electric fields generated by the electrodes.

In some embodiments, a distance sensor (not shown) may provide feedback to control module 8 or a user. Other sensors may be used, such as fluid flow sensors or impedance sensors, so that operating conditions can be measured and reported, in some cases to allow for changes to operating parameter values.

Distance D is not necessarily a positive distance in all ablation procedure models or ablation procedures. In some instances, electrode 18 or electrode 20 may be embedded in tissue 35 such that distance D has a negative value. In other ablation procedures, electrode 18 or electrode 20 may be held at the tissue surface such that distance D has a value of zero.

Figure 5:
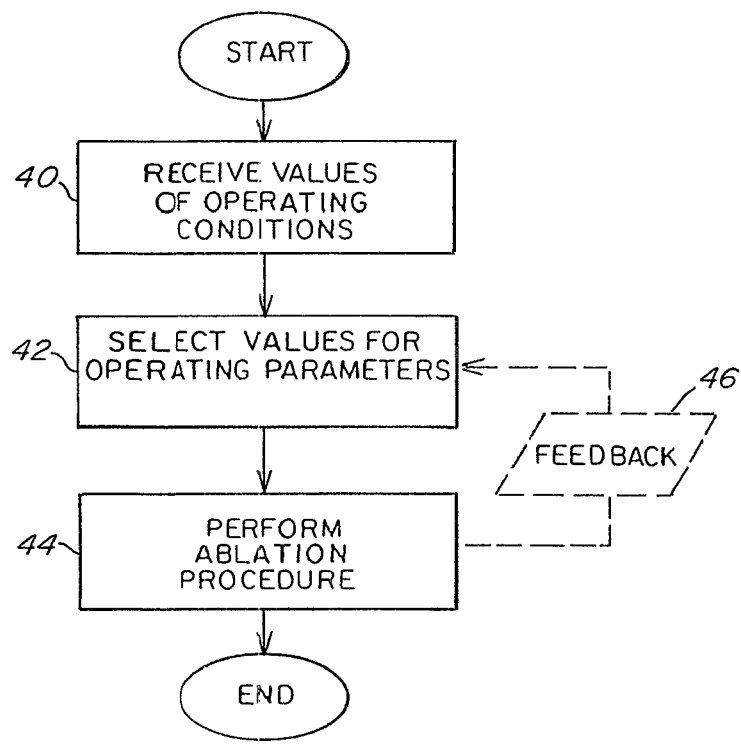
FIG. 5 illustrates one embodiment of a method of performing an ablation procedure.

Referring now to FIG. 5, one embodiment of a method of performing an ablation procedure is illustrated. In act 40, values of one or more operating conditions are received. In some embodiments, the values are represented by signals, such as electrical signals, which are input into a processor, a computer, or a control module. In other embodiments, the operating condition values are received visually by a user who may enter the values into a processor, a computer, or a control module. The user also may use the values in conjunction with charts, graphs, or tables without entering the values into a processor.

The values of the operating conditions may include values that attribute a certain level to an operating condition. For example, the operating condition value of "blood flow rate" may be "2.9 liters/minute." The values of the operating conditions also may include values that represent a selection from among a plurality of options. For example, the operating condition value of "electrode used" may be "7", which could represent a specific type or size of electrode having certain properties.

In act 42, values for one or more operating parameters are selected. The operating parameter values may be selected by a processor, a computer, a control module, or any other suitable device or set of instructions. In other embodiments, the operating parameter values may be selected by a user consulting charts, graphs or tables such as, for example, operation curves or lookup tables (see FIGS. 12 and 13).

A single value for a single operating parameter may be selected in act 42 in some embodiments of the method. In other embodiments, single values for more than one operating parameter may be selected substantially simultaneously. In still further embodiments, the selection of certain operating parameter values may be dependent on the value or values selected for other operating parameter(s).

Instead of a single value for an operating parameter being selected, a plurality of values may be selected such that each value corresponds to a different time during the ablation procedure. In some embodiments, the plurality of values may take the form of a continuum of values that vary over time. For example, a plurality of values for an operating parameter of electrode power may comprise a steadily decreasing power level over a period of sixty seconds.

In act 44, the selected operating parameter values are used in performing an ablation procedure. In some embodiments, not all of the selected values are used, particularly if certain operating parameters are not controllable or adjustable. In such embodiments, these operating parameters may instead be treated as operating conditions. In other embodiments, operating conditions that typically are not adjustable, but indeed are adjustable for a certain device or method, may be treated instead as operating parameters such that a value may be selected. For example, in one embodiment, the distance from a ring electrode surface to a tissue surface may not be adjustable, and thus the distance value is treated as an operating condition. In a different embodiment, the distance may be adjustable and thus may be treated as an operating parameter for which a value may be selected within certain boundaries.

Optionally, feedback 46 may be provided such that act 42 of selecting operating parameter values may be updated. For example, during act 44, the temperature of an ablation electrode may be measured. If the ablation electrode reaches a temperature of concern, based on the measurements, the power level being applied to the ablation electrode may be reduced. This act may take place automatically or with user intervention.

Figure 6:
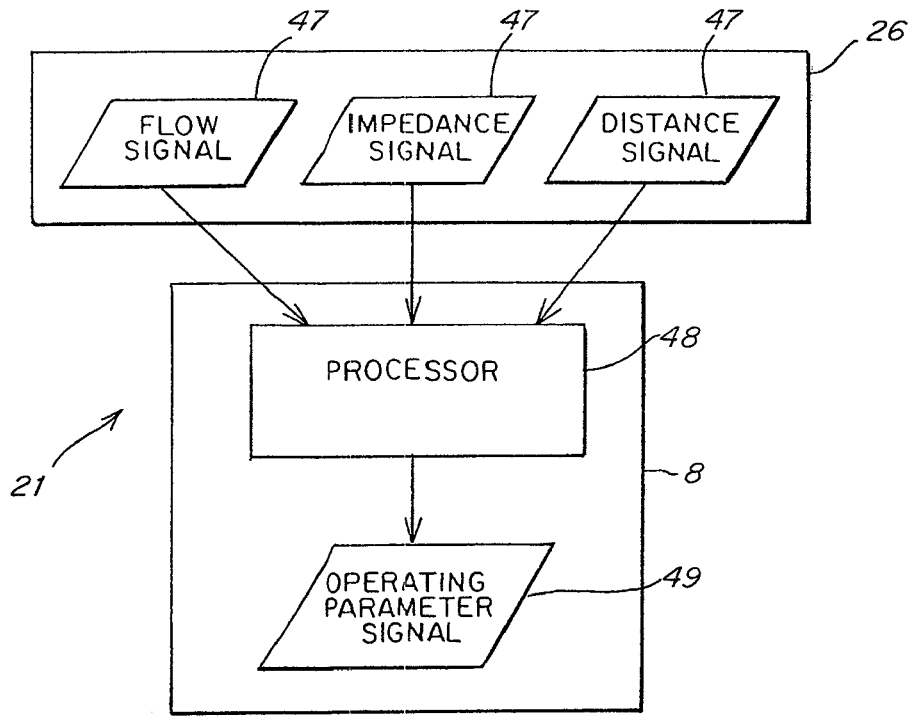
FIG. 6 illustrates one example of dataflow in a control system according to one embodiment of the invention.

Referring now to FIG. 6, one embodiment of a control system 21 for a catheter is illustrated. User interface module 26 is operatively connected to control module 8. Signals 47 representing operating parameter values and/or operating condition values are input at the user interface module and sent to a processor 48 for selection of a value for one or more operating parameters. A signal representing the selected value (operating parameter signal 49) is then output by processor 48. The selected value signal may be sent directly to the catheter, or the value may be displayed to the user such that the catheter may be controlled manually. Processor 48 may include operation curves or lookup tables, as described below. Processor 48 may interpolate when input values do not match the values present in a lookup value. Alternatively, processor 48 may include an equation or other algorithm to select an operating parameter value as a function of operating condition values.

Figure 7:
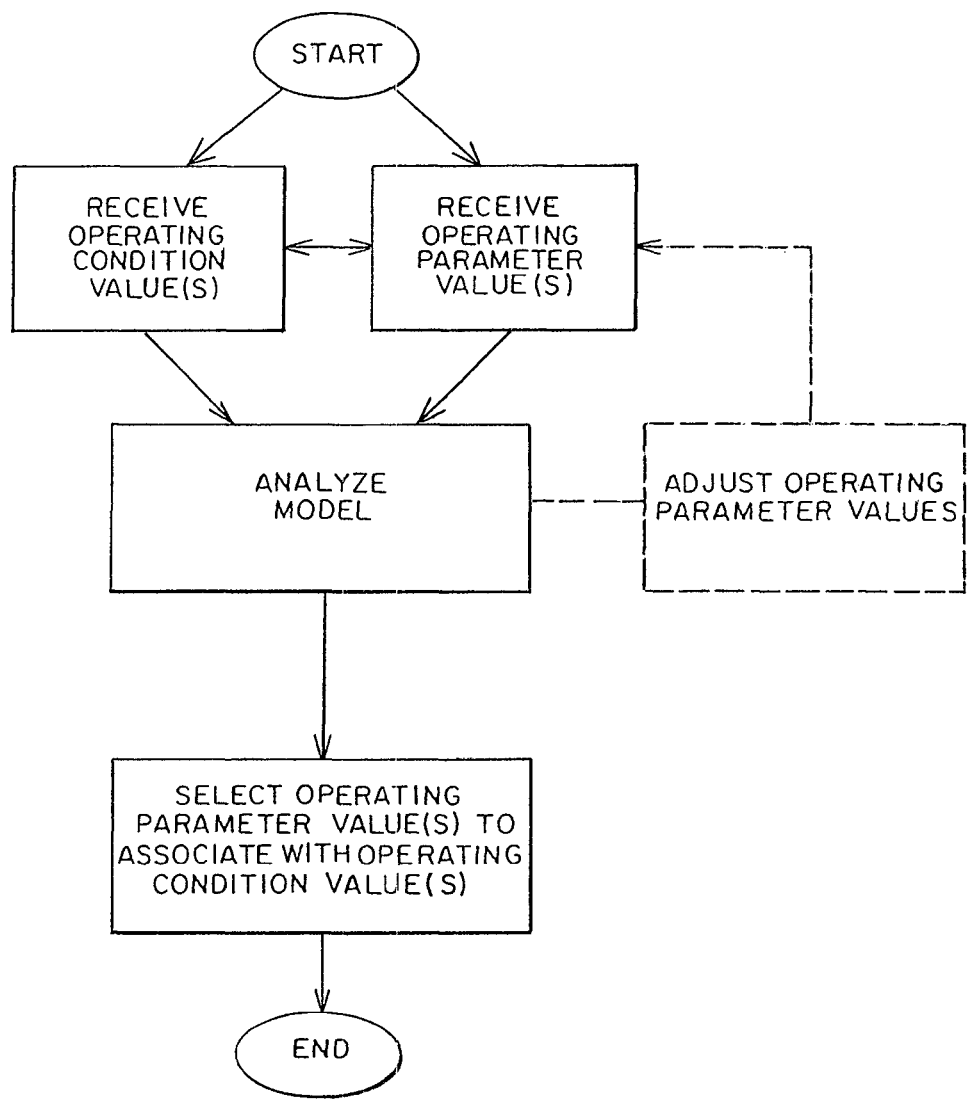
FIG. 7 illustrates one embodiment of a method of establishing relationships between operating condition values and operating parameter values.

Turning now to the groundwork for selecting suitable operating parameter values, one embodiment of a method of establishing a relationship between operating conditions and selected values for operating parameters is illustrated in FIG. 7. A model, such as a numerical model, may be used to estimate the results of an ablation procedure based on at least some of the following: values of various material characteristics; values of operating conditions and operating parameters; and electrical, thermal and flow equations.

Based on the results obtained by performing analyses of the model, values for adjustable operating parameters may be selected as a function of operating conditions or assumptions. For example, a certain blood flow rate, an electrode geometry and a distance from an electrode to a tissue surface may be provided as operating conditions for a series of model analyses. The results of selecting an initial value for an operating parameter, such as a power level applied to the electrode, may be modeled using the model and the operating condition values. After a first model analysis, results are recorded and a different power level may be used in a second model analysis. Based on the results of the two (or more) model analyses, a power level may be selected for use in an ablation procedure when the modeled operating conditions are encountered. This selection process is described in more detail below with reference to FIGS. 10 and 11.

Model Overview

Figure 8:
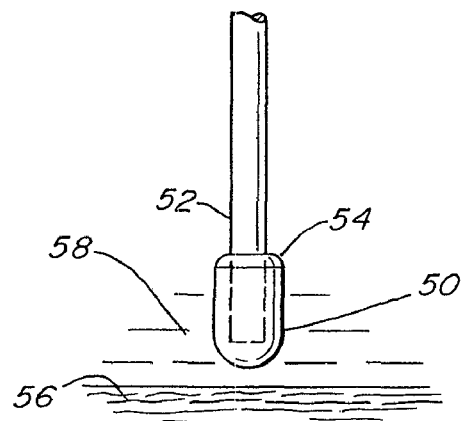
FIG. 8 illustrates components modeled in one embodiment of an ablation procedure model.

To model an ablation procedure, a finite element model may be constructed. In one exemplary model, the model includes an electrode 50, a plastic tip 52 of a catheter, epoxy 54 at the interface of electrode 50 and plastic tip 52, a tissue block 56 and a blood field 58 (see FIG. 8). Material properties are used as shown below by way of example in Table 1. Of course Table 1 shows just one example of a set of material properties that may be modeled and any suitable combination of various material properties may be modeled.

TABLE 1

| Part | Material | Density J/mm³ * K | Specific Heat g/mm³ | Thermal Conductivity W/mm * K | Electrical Conductivity S/mm | Thermal Diffusivity mm²/s |
|---|---|---|---|---|---|---|
| Blood | Blood (viscosity 0.001 g/s mm) | 0.0010 | 4.180 | 0.000543 | 6.670E-=04 | 0.13 |
| Epoxy | | 0.0013 | 1.500 | 0.00130 | 1.000E-13 | 0.07 |
| Tip | Pebax[1] | 0.0010 | 5.500 | 0.000290 | 1.072E-17 | 0.05 |
| Electrode | Platinum | 0.0215 | 0.132 | 0.071000 | 4.000E+3 | 25.02 |
| Tissue | Cardiac Muscle | 0.0012 | 3.220 | 0.0005367 | 2.220E-04 | 0.14 |

[1]80% Pebax 6333/20% Barium Sulfate, Panton 548C

Boundary conditions may be set as follows: outer surface—zero volts and 37° C.; electrode surface—25 volts to 75 volts; tissue fluid interface—no slip (U=0, V=0, W=0); electrode fluid interface—no slip (U=0, V=0, W=0); inlet flow—U=10.4 mm/sec, 30 mm/sec, or 52 mm/sec depending on flow conditions, V=0, W=0; outer boundaries—no slip (U=0, V=0, W=0). The initial temperature of the model is set to 37° C. The above boundary conditions are assumptions and different assumptions may be used for various models.

Figure 9:
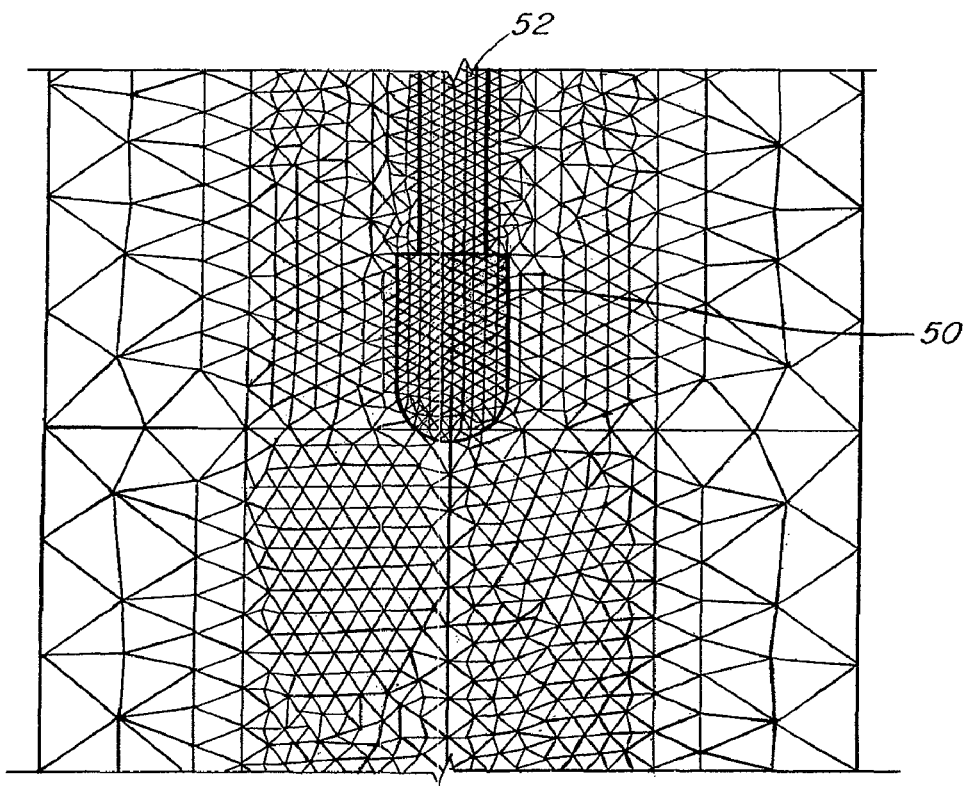
FIG. 9 illustrates a portion of a mesh used in one embodiment of a finite element model.

The model includes a finite element mesh that is partitioned along the catheter length with a finer mesh in the area of the electrode. An illustration of a portion of the mesh is shown in FIG. 9. The mesh grading in this illustration is 3.00 mm×1.00 mm×0.30 mm and includes 22,914 nodes. Because of the geometry symmetry, half of the geometry may be used. As is known to one of ordinary skill in the art, various mesh gradations may be used in constructing a finite element model.

In the model, the electric potential $\psi$ is solved at each time step using Laplace's equation:

$$\nabla \cdot \sigma \nabla \phi = 0 \tag{1}$$

The joule heat generation term, $$J \cdot E = \sigma \cdot \|\nabla \cdot\|^2, \tag{2}$$

is calculated and added to the right hand side of the energy equation:

$$\rho c \left( \frac{\delta T}{\delta t} + U \frac{\delta T}{\delta x} + V \frac{\delta T}{\delta y} + W \frac{\delta T}{\delta z} \right) = \nabla \cdot (k \nabla T) + J \cdot E. \tag{3}$$

To model the fluid flow, the velocity distribution was solved using the momentum equations:

$$\rho \left( \frac{\delta U}{\delta t} + U \frac{\delta U}{\delta x} + V \frac{\delta U}{\delta y} + W \frac{\delta U}{\delta z} \right) = -\frac{\delta P}{\delta x} + \mu \left( \frac{\partial^2 U}{\partial x^2} + \frac{\partial^2 U}{\partial y^2} + \frac{\partial^2 U}{\partial z^2} \right) \tag{4}$$

$$\rho \left( \frac{\delta V}{\delta t} + U \frac{\delta V}{\delta x} + V \frac{\delta V}{\delta y} + W \frac{\delta V}{\delta z} \right) = -\frac{\delta P}{\delta y} + \mu \left( \frac{\partial^2 V}{\partial x^2} + \frac{\partial^2 V}{\partial y^2} + \frac{\partial^2 V}{\partial z^2} \right) \tag{5}$$

$$\rho \left( \frac{\delta W}{\delta t} + U \frac{\delta W}{\delta x} + V \frac{\delta W}{\delta y} + W \frac{\delta W}{\delta z} \right) = -\frac{\delta P}{\delta z} + \mu \left( \frac{\partial^2 W}{\partial x^2} + \frac{\partial^2 W}{\partial y^2} + \frac{\partial^2 W}{\partial z^2} \right), \tag{6}$$

and the continuity equation:

$$\frac{\delta U}{\delta x} + \frac{\delta U}{\delta y} + \frac{\delta U}{\delta z} = 0. \tag{7}$$

The energy equation (Eq. 3) is then solved for the temperature distribution in the tissue.

In the above equations:
p represents density (k/mm³);
c represents specific heat (J/g*K)
k represents thermal conductivity (W/mm*K)
J represents current density (A/mm²)

E represents electric field density (V/mm$^2$)

T represents temperature

U, V, W represent fluid velocity components (mm/sec)

σ represents electrical conductivity S/mm

φ represents electrical potential.

Model Results

A graph showing the results of examples of model analyses is shown in FIG. 10. The y-axis shows the modeled power level (watts) and the x-axis shows the maximum tissue temperature (degrees C) reached during the model analysis. This model had a blood flow rate operating condition of 30 mm/sec and a distance of D of −0.009 inches. Ten different electrodes were analyzed, each at four different power levels.

By fitting a curve to the results for each electrode, a power level at which the maximum tissue temperature will reach a pre-determined level may be estimated. For example, according to a curve 62 fit to the model analysis results, a 7F Distal Morgan 8 mm electrode sustained at a power level of approximately 41 watts or less for 60 seconds will result in a maximum tissue temperature of approximately 95° C. or less. A modeled temperature such as 95° C. or 90° C. may be used as a cutoff to allow for a safety factor below 100° C. Typically, a higher maximum tissue temperature results in a larger lesion. Thus, to achieve maximum lesion size within the operating conditions of a blood flow rate of 30 mm/sec, a distance D of −0.009 inches, and a 7F Distal Morgan 8 mm electrode, a power level of 41 watts is selected, which is predicted to result in a maximum tissue temperature of approximately 95° C.

FIG. 11 illustrates a graph that plots another operating parameter value versus maximum tissue temperature. This graph shows model analysis results for different maximum electrode temperature levels. Instead of having its power level controlled, an ablation electrode can have its maximum temperature controlled. Based on a curve 64 fit to the model analysis results shown in FIG. 11, a maximum electrode temperature of approximately 53° C. is selected to maximize lesion size while keeping the modeled maximum tissue temperature below 95° C. when operating conditions of a blood flow rate of 30 mm/sec, a distance D of −0.009 inches and a 7F Distal Morgan 8 mm electrode are present.

Figure 12A:
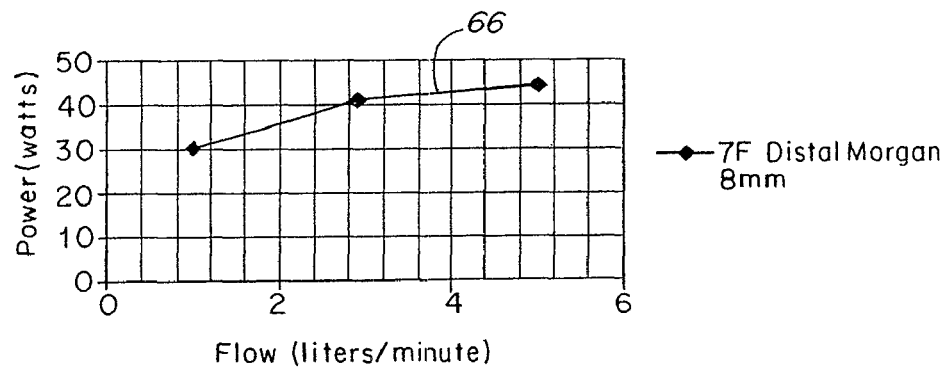
FIGS. 12A and 12B illustrates exemplary operation curves generated from model analyses.
Figure 12B:
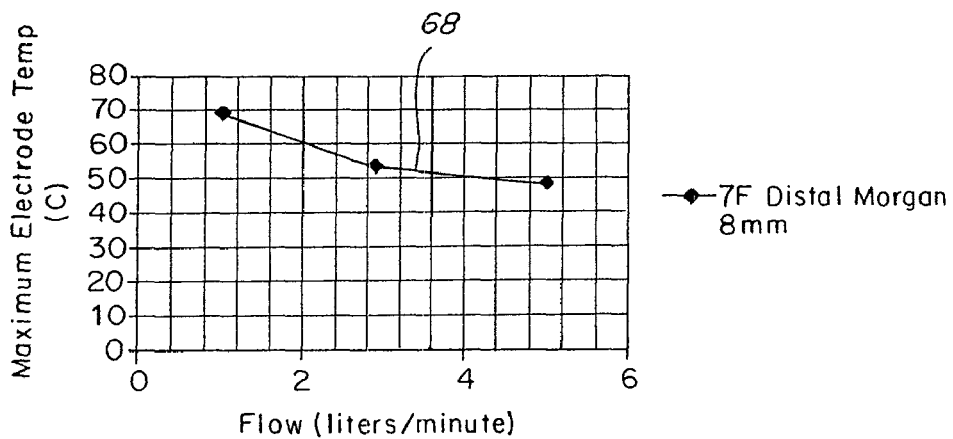

Once analyses have been performed for several different values of an operating condition and operating parameter values have been selected for these operating conditions, operation curves may be generated, such as the ones shown by way of example in FIGS. 12A and 12B. Graph 66 plots electrode power vs. flow, and graph 68 plots maximum electrode temperature vs. flow. When performing an ablation procedure, a user may refer to an operation curve to select an appropriate power level as a function of a given blood flow rate, a given distance from electrode to tissue surface, and a selected electrode. If instead the user decides to control voltage or maximum electrode temperature, those curves could be provided on a separate graph or could be provided on the same graph. It is important to note that for purposes herein, the phrase "as a function of" certain values does not preclude the use of further values. For example, "as a function of a blood flow rate" does not preclude the use of other values such as impedance, voltage, etc.

Figure 13:
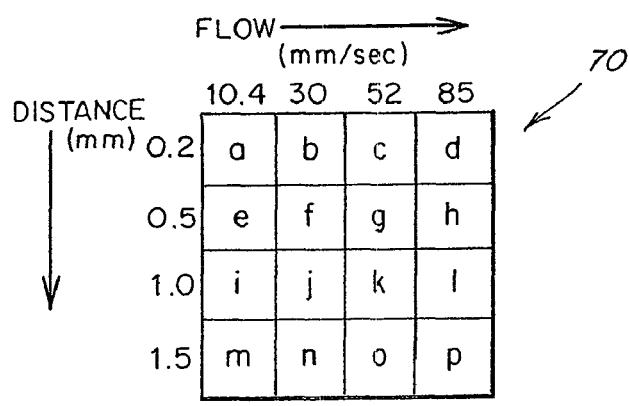
FIG. 13 illustrates a format for lookup tables according to one embodiment of the invention.

In an alternative embodiment, lookup tables may be provided instead of operation curves. An example of a lookup table 70 is shown in FIG. 13. Table 70 is titled, "Electrode A", and using a given flow rate and distance, an appropriate operating parameter value (represented by lower case letters a-p) may be selected. Of course, lookup tables may be arranged by flow or distance or other operating condition and the assignment of parameters and conditions to columns and rows may vary.

An automated optimization scheme may be employed to systematically analyze different types of modeled electrodes and different modeled distances between the electrode and the tissue surface. For each set of values for operating conditions (such as blood flow rate) and operating parameters (such as power level or distance from electrode to tissue surface), a model analysis provides a lesion size. Based on the results of the model analysis, an optimization module may select a new set of operating parameter values and determine whether the model predicts a larger or smaller lesion size. Any suitable optimization scheme known in the art may be used to complete the optimization process. As is known to those of ordinary skill in the art, many optimization schemes do not necessarily produce a single optimal result, but rather attempt to locate a result as close as possible to an optimal result given computational constraints.

For a given operating condition (such as blood flow rate), a number of sets of operating parameter values can be selected. For example, for a given operating condition valve, a first set of operating parameter values such as a first electrode, a first distance D, and a second power level may be presented as a suitable option. The presentation of multiple suitable sets operating parameter values may be desirable when certain electrodes are not available or other restrictions are present. Attributes of the model analysis results could also be presented for each set, such as robustness in light of perturbations.

Instead of, or in addition to model analysis, actual experiments can be used to generate the operating curves and/or lookup tables for various combinations of the input values. In some embodiments, in vitro experiments may be used to generate data for the operating curves.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of selecting an operating parameter value for supplying energy to an ablation electrode, comprising:
   (a) receiving a first signal representing a value of a fluid flow rate;
   (b) receiving a second signal representing a value of an impedance;
   (c) receiving a third signal representing a value of a positive distance from an ablation electrode surface to a target tissue surface; and
   (d) selecting a value for an operating parameter for supplying energy to the ablation electrode as a function of the first, second and third signals;
   wherein:
   (d) comprises selecting the operating parameter value based on relationships established between (1) values of the operating parameter and (2) fluid flow rate values, impedance values and distance values;
   the relationships are established with analyses of a numerical model of transmission of energy to biological tissue by an ablation electrode;
   the numerical model comprises a finite element model; and
   to model a tissue temperature distribution, the numerical model comprises equations for modeling an electric field created by the ablation electrode, heat generated by the electric field, and a velocity field of the fluid flow.

2. The method according to claim 1 wherein the numerical model comprises the following equations to model tissue temperature distribution:

$$\nabla \cdot \sigma \nabla \varphi = 0;$$

$$\rho c \left( \frac{\delta T}{\delta t} + U \frac{\delta T}{\delta x} + V \frac{\delta T}{\delta y} + W \frac{\delta T}{\delta z} \right) = \nabla \cdot (k \nabla T) + J \cdot E;$$

$$\rho \left( \frac{\delta U}{\delta t} + U \frac{\delta U}{\delta x} + V \frac{\delta U}{\delta y} + W \frac{\delta U}{\delta z} \right) = -\frac{\delta P}{\delta x} + \mu \left( \frac{\partial^2 U}{\partial x^2} + \frac{\partial^2 U}{\partial y^2} + \frac{\partial^2 U}{\partial z^2} \right);$$

$$\rho \left( \frac{\delta V}{\delta t} + U \frac{\delta V}{\delta x} + V \frac{\delta V}{\delta y} + W \frac{\delta V}{\delta z} \right) = -\frac{\delta P}{\delta y} + \mu \left( \frac{\partial^2 V}{\partial x^2} + \frac{\partial^2 V}{\partial y^2} + \frac{\partial^2 V}{\partial z^2} \right);$$

$$\rho \left( \frac{\delta W}{\delta t} + U \frac{\delta W}{\delta x} + V \frac{\delta W}{\delta y} + W \frac{\delta W}{\delta z} \right) = -\frac{\delta P}{\delta z} + \mu \left( \frac{\partial^2 W}{\partial x^2} + \frac{\partial^2 W}{\partial y^2} + \frac{\partial^2 W}{\partial z^2} \right);$$

and $$\frac{\delta U}{\delta x} + \frac{\delta U}{\delta y} + \frac{\delta U}{\delta z} = 0.$$

3. The method according to claim 1, wherein the relationships are established with analyses of an in vitro model of transmission of energy to biological tissue by an ablation electrode.

4. The method according to claim 1, wherein the second signal, representing the value of the impedance, comprises a signal representing an electrode geometry.

5. The method according to claim 1, wherein the second signal, representing the value of the impedance, represents an impedance into which energy is supplied.

6. The method according to claim 1, wherein (d) comprises selecting a plurality of values for an operating parameter, each value corresponding to a separate time during the supplying of energy to the ablation electrode.

7. The method according to claim 1, wherein (d) comprises selecting a value for each of a plurality of operating parameters.

8. The method according to claim 1, wherein the operating parameter is a maximum temperature allowed for the ablation electrode.

9. The method according to claim 1, wherein the operating parameter is power applied to the ablation electrode.

10. The method according to claim 1, wherein the operating parameter is voltage of the energy supplied to the ablation electrode.

11. The method according to claim 1, wherein (d) comprises selecting the operating parameter value using a processor programmed with an algorithm.

12. The method according to claim 1, wherein (a) comprises receiving the first signal from a fluid flow sensor.

13. The method according to claim 1, wherein the first signal is generated by an input entered by a user.

14. The method according to claim 1, wherein (b) comprises receiving the second signal from an impedance sensor.

15. The method according to claim 1, wherein (c) comprises receiving the third signal from a distance sensor.

16. A method of supplying energy to an ablation electrode comprising the method of claim 1 and further comprising:
(e) controlling an energy supply such that energy is supplied to the ablation electrode at the selected operating parameter value.

17. The method according to claim 1, wherein the first signal, representing a value of a fluid flow rate, represents a value of a blood flow rate.

18. The method according to claim 17 wherein (d) comprises selecting the operating parameter value based on relationships established between (1) values of the operating parameter and (2) blood flow rate values, impedance values and distance values.

19. The method according to claim 18, wherein the relationships are established with analyses of a numerical model of transmission of energy to biological tissue by an ablation electrode.

20. The method according to claim 19 wherein the numerical model comprises a finite element model.

* * * * *